United States Patent [19]

Steffen

[11] Patent Number: 5,334,747

[45] Date of Patent: Aug. 2, 1994

[54] METHOD OF PREPARING SUBSTITUTED MALONIC ESTER ANILIDES AND MALONIC ACID MONO-ANILIDES

[75] Inventor: Klaus-Dieter Steffen, Hennef, Fed. Rep. of Germany

[73] Assignee: Huls Aktiengesellschaft, Marl, Fed. Rep. of Germany

[21] Appl. No.: 864,740

[22] Filed: Apr. 7, 1992

[30] Foreign Application Priority Data

May 6, 1991 [DE] Fed. Rep. of Germany ....... 4114733

[51] Int. Cl.$^5$ ............................................ C07C 229/40
[52] U.S. Cl. ............................................ 560/43; 560/9; 560/22; 562/426; 562/437; 562/455; 562/456; 564/134; 564/135; 564/155; 564/157
[58] Field of Search ............... 562/456, 426, 437, 455, 562/456; 560/9, 22, 43; 564/134, 135, 155, 157

[56] References Cited

U.S. PATENT DOCUMENTS 4,443,624 4/1984 Prange et al. .................. 560/204
5,123,951 6/1992 See et al. ........................ 71/86

FOREIGN PATENT DOCUMENTS 0394440 10/1990 European Pat. Off. .
8705898 10/1987 PCT Int'l Appl. .

OTHER PUBLICATIONS

Halogen Derivatives of Malonanilide, Ethyl Malonanilate and Malonanilic Acid; F. D. Chattaway et al. (J. Chem. Soc. 97, 339 1919).
Chemical Abstracts, vol. 109, No. 9, Aug. 28, 1988, Columbus, Ohio, US; Abstract No.68759d, N. Shindo et al. "Plant growth regulating properties of alkyl 2-(-phenylcarbamoyl)propionates", p. 257 & Meiji Daigaku Nogakubu Kenkyu Hokoku No. 78, 2988, pp. 75-91.
Tetrahedron, (Incl. Tetrahedron Reports) vol. 44, No. 8, 1988, Oxford GB. pp. 2351-2358; F. Maran et al. "Electro-Carboxylation of 2-Bromoisobutyramides. A Useful Synthetic Way to Ester-Amides of 2,2-*Dimethylmalonic Acid*", p. 2357, Col. 39.
Patent Abstracts of Japan, vol. 10, No. 292 (c-376) (2348) Oct. 3, 1986 & JP-A-61 109 769.
Chemical Abstracts, vol. 87, No. 7, Aug. 15, 1977, Columbus, Ohio, US; Abstract No. 52961e, T. Mukai et al. "Phenylcarbamic acid ester", p. 438 & JP-A-77 014 745 (Yoshitomi Pharmaceutical Ind.).

*Primary Examiner*—José G. Dees
*Assistant Examiner*—Samuel Barts
*Attorney, Agent, or Firm*—Sprung Horn Kramer & Woods

[57] ABSTRACT

Malonic mono-ester mono-anilides and malonic acid mono-anilides and bis-anilides are produced by reaction of malonic acid di-alkyl esters with an aniline in the presence of a stoichiometric amount, based on the aniline, of an alkali alcoholate, accompanied by the initial formation of alkali salts of mono-ester mono-anilides or malonic-acid bis-anilides. Neutralization results in the formation of free malonic mono-ester mono-anilide or malonic-acid bis-anilide and saponification forms the malonic acid mono-anilide. Chloro-substituted anilides of cyclopropyl-1,1-dicarboxylic acid and their mono-esters are preferred.

8 Claims, No Drawings

METHOD OF PREPARING SUBSTITUTED MALONIC ESTER ANILIDES AND MALONIC ACID MONO-ANILIDES

The invention involves the preparation of either mono-ester mono-anilides, mono-acid mono-anilides, or bis-anilides of singly or doubly substituted malonic acids, of the general formula

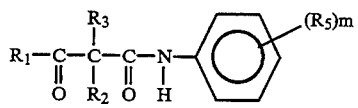

(I)

by reacting singly or doubly substituted malonic-acid di-alkyl esters of the formula

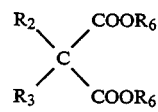

(II)

with amines of the formula

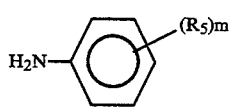

(III)

through the addition of alkali alcoholates.

Although the alkali salts of the anilines of Formula (III) are not unknown (Houben-Weyl 11, 2, p. 182), little attention has been paid to them. They are easy to obtain from the aniline and alkali alcoholate in accordance with the invention.

Malonic mono-ester mono-anilides and malonic-acid mono-anilides are prepared in the sequence

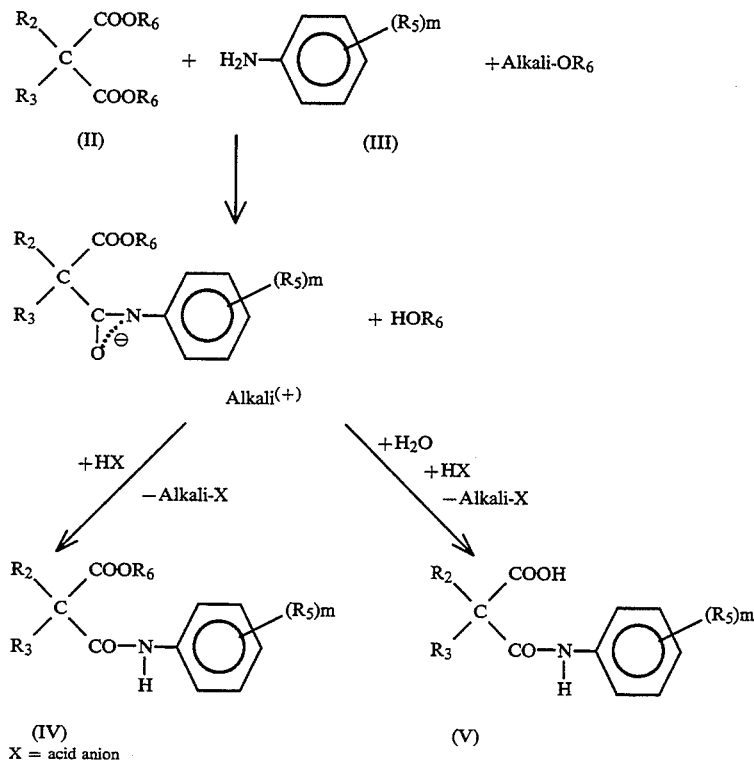

X = acid anion

In Formulas (I) through (V),
$R_1 = $O-alkyl $(C_1-C_6)$, OH, O$^-$ alkali$^+$, or

[NH—aryl structure with $(R_5)_m$]

$R_2 = $alkyl $(C_1-C_6)$, alkoxy $(C_1-C_6)$, or aryl,
$R_3 = $H, alkyl $(C_1-C_6)$, alkoxy $(C_1-C_6)$, or aryl,
$R_2 + R_3 = $—$(R_4CR_4)_n$—, where n=2-5,
$R_4 = $H, $CH_3$, or halogen,
$R_5 = $halogen, alkyl $(C_1-C_6)$, alkoxy $(C_1-C_6)$, $N(R_6)_2$, cyano, acyl, nitro, or thio-alkyl $(C_1-C_6)$,
m=0-5, and
$R_6 = $alkyl $(C_1-C_6)$.

Compounds of Formula (I) are not unknown and are used as plant-growth regulators (WIPO 87/05781), to increase the yields of beans (WIPO 87/05897) for example, or to decelerate the growth of grass or trees (WIPO 87/05898). In those contexts the preparation proceeds from unsubstituted malonic esters ($R_2 = R_3 = H$) by unilateral saponification, obtaining the acid chloride, reacting with amine, and introducing the substituent $R_2$ or $R_3$. This multistage route is complicated and its yields are low. In Example 22 of WIPO 87/05898 for instance, di-ethyl malonate is reacted directly with 4-chloroaniline, and the yield of malonic acid monoethylester mono-(4-chloroanilide) is only 20%.

Similarly low yields of 28.7% of malonic acid bis-(3,4-dichloroanilide) have been obtained by boiling diethyl malonate with 3,4-dichloroaniline for 18 hours (D. J. Beaver et al., JACS 79 [1957], 1236).

The conventional conversion of esters and amines into the corresponding acid amides with $NH_4Cl$ as a catalyst is no improvement. Even catalytic quantities of alkali alcoholate have only a negative effect if any on the course of the reaction and on the purity of the final product.

F. D. Chattaway et al. (J. Chem. Soc. 97, 339) convert unsubstituted malonic acid diethyl ester with various halo-anilines at boiling heat (199° C. for DEM) into the mono- and bis-halo-anilides. Under these conditions, both the bis-anilide and mono-anilide of malonic acid are obtained. Although diethyl malonate is even added in an excess of 50% relative to the halo-aniline, however, purity and yield are unsatisfactory, the only yield cited being 20%.

Thus, according to the state of the art, anilides of the substituted or unsubstituted malonic ester and acid are obtained from anilines and malonic esters only in low yields and purity.

It is accordingly an object of the present invention to increase the specificity of the reaction and to definitely improve the yield and purity of the product.

This object is realized in accordance with the invention by directly reacting malonic ester (II) with aniline (III) to form the corresponding malonic mono-ester mono-anilide (IV). Surprisingly, high yields, some of well over 90%, of high-purity mono-ester mono-anilides are obtained by use of alkali alcoholate.

It is preferable initially to obtain the alkali salt of aniline (III) from the particular aniline and an alkali metal alcoholate or alkaline earth metal alcoholate and then to react it with the malonic acid dialkyl ester (II).

The alkali salts of aniline (III) make it possible to carry out the reaction at definitely lower temperatures than at the state of the art, specifically at 0° to 150° C. and preferably at 10° to 50° C. and the after-reaction at 50° to 150° C. Again, the alkali salts of malonic mono-ester mono-anilides (IV) will also form complete and pure in this approach in a simple reaction. The amount of alkali alcoholate should essentially be stoichiometric in terms of aniline (III), but an excess will be neither harmful nor beneficial. 85 to 130%, preferably 95 to 110%, and especially preferably for practical purposes 99 to 105% molar of the alkali alcoholate in terms of aniline (III) can be employed. Tests like those described in Example 1 hereinbelow have indicated that decreasing the amount of alcoholate to 80% molar and less will result in lower and lower yields of an increasingly impure malonic mono-ester mono-anilide (IV). The malonic ester is added in 95 to 105% of the stoichiometric quantity of the aniline. The alkali salts of anilines (III), especially the chloroanilines, can be obtained just by heating the aniline with a solution or suspension of alkali alcoholate in alcohol. As the batch cools, large crystals of the alkali anilides precipitate and can be harvested. These crystals are almost 100% pure (as determined by perchloric acid titration, sodium detection, and gas chromatography).

The alkali alcoholates are accordingly added preferably in an non-aqueous solution and highly preferably in a solution of the particular associated alcohol. Appropriate alcoholates are sodium or potassium alcoholates of the aliphatic alcohols with 1 to 6 carbon atoms, e.g. $NaOCH_3$, $KOCH_3$, $NaOC_2H_5$, K-t-butylate, and $Mg(OR_6)_2$. The alkali salt of aniline (III) can be added as a solid or in solution with singly or doubly substituted malonic ester (II) in any sequence. If the alkali salt of the aniline is prepared in solution, the malonic ester can be added in the same vessel.

Additional solvents, such aliphatic hydrocarbons for example as heptane, hexane and cyclohexane, such aromatic hydrocarbons as toluene or xylene, and ether, t-butyl methylether for example, may also be present during the reaction.

The reaction commences at room temperature and continues with low heat tonality. Temperatures above 30° C. result in side products and should be avoided. The reaction is completed by briefly warming the batch, from which all or some of the alcohol will separated from the condensing anilide by distillation as additional solvents are added, often in the form of an azeotrope with methyl alcohol, optionally under reduced pressure, and the mixture of solvent and alcohol can be separated and used again.

The alkali salt of the particular malonic mono-ester mono-anilide (IV) is now present molten, suspended or dissolved in a solution from which it can be precipitated out by cooling. Filtering will purify it by removing any remaining starting materials or contaminants.

Then as much of acids such as hydrochloric, sulfuric, acetic or formic acid as there is alkali present is now added to the alkali salt of malonic mono-ester mono-anilide (IV) or to its suspension in solvents to neutralize it. The alkali salts of the added acids are dissolved in water and the free anilide precipitated from the aqueous salt solution separated by filtration or phase-separation and washed to yield the product. It is also possible to follow the neutralization with filtering the reaction mixture along with the solvent from the precipitated alkali salt (e.g sodium chloride) and distilling off the solvent while crystallizing or vacuum distilling the anilide out of it.

It is also possible in accordance with the invention initially to prepare mono-ester mono-anilides and obtain mono-acid mono-anilides of the singly or doubly substituted (i.e. with $R_2$ and $R_3$) malonic acids therefrom in the same way without intermediate isolation of the preliminary stage. A specific number of anilides (I), however, are employed as agricultural chemicals as described in the aforesaid WIPO documents and preferably prepared in accordance with the invention, specifically preparing mono- and bis-anilides with chlorine substituents on the one hand and any desired anilides of such malonic acids or esters wherein groups $R_2$ and $R_3$ jointly constitute the group $—(R_4CR_4)_n—$, wherein $n=2-5$, bonded to the middle carbon of the malonic acid and in particular a cyclopropane or cyclobutane ring that can contain methyl groups or chlorine. Also preferred are the anilide of mono- or di-alkylmalonic acid or its mono-ester, wherein alkyl=$C_1$ to $C_2$. Very preferred are cyclopropyl-1,1-dicarboxylic acid mono-anilides and di-anilides or mono-ester mono-anilides wherein $R_5$=chlorine and $m=1-3$. To prepare malonic-acid anilides (V), the alkali salt of malonic mono-ester mono-anilide.(IV) or, preferably, the alkaline reaction mixture itself, is added to water and the ester group saponified into the acid group. This can be done by stirring at room temperature or by refluxing for several hours. To improve saponification it will sometimes be necessary to add catalysts, phase-transfer catalysts for example. The precise reaction conditions for complete saponification can be determined while the process is going on by analyzing samples.

Once saponification is complete, once the pH of the aqueous solution has dropped from approximately 14 to approximately 10, that is, the organic phase, which consists of the solvent, toluene or heptane for example, and of color-producing contaminants, is separated and the aqueous phase is acidified to a pH of 2 with an acid such as hydrochloric acid. The aqueous, alkaline phase can be filtered clear to eliminate any insoluble by-products before acidification. The phase can be additionally purified with a fresh solvent, toluene, heptane or cyclohexane for instance, that does not mix with water. These organic solvent phases can be employed again for subsequent batches, with any traces of water removed by brief azeotropic distillation or even by such dry approaches as molecular sieves.

The precipitated product, malonic acid anilide (V) usually precipitates as crystals. It is filtered out, washed and dried, needing no subsequent purification.

When the malonic acid anilide (V) is a liquid, it is separated and distilled pure in a vacuum. The products accordingly obtained in two steps and in yields of 85% to 90% of theoretical in terms of malonic ester (II), are 95% to 100% pure.

Bis-anilides (I) occur to some extent, depending on how the reaction is carried out, in small quantities along with the mono-anilides and can be separated from the aqueous phase subsequent to the alkaline saponification of the mono-ester mono-anilides, before the acids are added, that is. Bis-amides free of mono-amides can be obtained by reacting two aniline-and-alkali-salt equivalents.

Alkali salts also, i.e. mono-alkali salts of mono-ester anilides and, by saponifying them when desired, di-alkali salts of mono-acid mono-anilides, can be obtained by removing the organic phase and concentration or by adding more alkali. Mono- or di-alkali salts of bis-anilides can be obtained by removing the organic phase and incomplete neutralization or none. Highly preferred alkali salts are the sodium salts.

In accordance with the invention there are also provided new compounds, viz. those of the formulas

[Structural formulas shown]

wherein
$R_7 = CH_3$ or $C_2H_5$,
$R_8 = H$, $CH_3$ or $C_2H_5$
$n = 1$ to 3
$R_9 = $ alkali, H, $CH_3$, $C_2H_5$ or

[Structural formula shown]

Alkali = sodium or potassium, and
$p = 1$ to 5.

EXAMPLE 1

Cyclopropyl-1,1dicarboxylic-acid mono-(2,4-dichloro)-anilide || [cyclopropyl-1-(2,4-dichlorophenylamino) carbonyl-1-carboxylic acid]

79.3 g of a 30% by weight solution of sodium methanolate (0.44 mole), 64.8 g of 2,4-dichloroaniline (DCA, 0.4 mole), and 300 ml of toluene are placed in a 1.5-1 four-necked flask equipped with a thermometer, mixer, short column and distillation section, and heated to the boiling point. The azeotrope of methyl alcohol and toluene is distilled off until the overhead temperature reaches 110° C. (90 g of distillate).

The batch is allowed to cool to 20° C., 63.2 g of cyclopropyl-1,1-dicarboxylic-acid dimethyl ester (CDM, 0.4 mole) are added while the batch is being stirred. The temperature increases to 35° C. The stirring is continued at room temperature for 1 hour. The methyl alcohol and toluene are removed azeotropically and the batch boiled for another 1.5 hour, then is cooled. 500 ml of water are added. The ester group is saponified by heating to the boiling point for 3.5 hours.

The batch is cooled. The organic toluene phase is separated from the aqueous phase, which has a pH of 10 to 11. The aqueous solution is filtered and acidified to a pH of 3 with hydrochloric acid. The product, a white precipitate, is filtered off, washed with water and vacuum dried at 100° C.

Weight: 97.8 g (89.2% of theory based on CDM)
Melting point: 192°–193.5° C.
Purity (HPLC): 98.6%.

The toluene phase (150 g) contains 0.8 to 0.9% 2,4-dichloroaniline, traces of cyclopropyl-1,1-dicarboxylic acid dimethyl ester, and unsaponified cyclopropyl-dicarboxylic acid mono-methyl ester mono-dichloro-anilide. The phase is dried on beads of a molecular sieve and employed in the following examples.

EXAMPLES 2 AND 3

Cyclopropyl-1,1-dicarboxylic acid mono-(2,4-dichloro)-anilide 79.3 g of 30% by weight of solution of sodium methanolate (0.44 mole) is placed in the container described in Example 1 with only 63.7 g of 2,4-dichloroaniline and 125 g of the toluene phase separated in Example 1 and containing another 1.1 g of 2,4-dichloroaniline. 155 ml (left over from the 300) of fresh toluene are also added.

The methyl alcohol is distilled off. 63.2 g (0.4 mole) of cyclopropyl-1,1-dicarboxylic acid dimethyl ester are added at room temperature, and the reaction is continued as described in Example 1 to obtain the desired product.

Weight: 96.8 g (88.3% of theory based on CDM)
Melting point: 192°–193° C.
Purity (HPLC): 98.6%

In Example 3, the toluene phase separated in Example 2 and still containing 1.5 g of 2,4-dichloroaniline, is used again with 63.3 g of fresh 2,4-dichloroaniline and another 200 ml of fresh toluene.

The reaction is conducted as described in Examples 1 and 2.

Weight: 96.8 g (88.3% of theory based on CDM)
Melting point: 191°–193° C.
Purity (HPLC): 98.4%

EXAMPLE 4

Cyclopropyl-1,1-dicarboxylic acid mono-methyl ester mono-(2,4-dichloro)-anilide ‖ [cyclopropyl-1-(2,4-dichlorophenylamino)-carbonyl-1-carboxylic acid methyl ester] and its sodium salts a) 79.3 g (0.44 mole) of a 30% by weight solution of NaOCH$_3$, 64.8 g (0.4 mole) of 2,4-dichloroaniline, and 500 ml of cyclohexane are placed in a 1.5-1 four-necked flask equipped with a thermometer, mixer, short column and distillation section, and heated to the boiling point. All the methyl alcohol is distilled off azeotropically at a boiling point of 55° C. The batch is cooled to room temperature. 63.2 g (0.4 mole) of cyclopropyl-1,1-dicarboxylic acid dimethyl ester and 200 ml of cyclohexane are added. The batch is heated 1.5 hours until all the by-product methyl alcohol has distilled off. The batch is cooled and the precipitate—sodium salt of cyclopropyl-1,1-dicarboxylic acid monomethyl ester mono-(2,4-dichloro)-anilide—filtered out, washed with cyclohexane, and dried.

Weight: 119.4 g (96.3% of theory) of $C_{12}H_{10}Cl_2NO_3Na$ (MW 310.11)

|       | C    | H   | N   | O    |
|-------|------|-----|-----|------|
| Calc: | 46.5 | 3.3 | 4.5 | 15.5 |
| Found:| 46.4 | 3.4 | 4.5 | 15.3 |

Melting point: >220° C. (disintegration)

b) 115 g of the sodium salt from step a) are rapidly dissolved in 1 l of cold water (pH=13–14) while simultaneously stirred and acidified to a pH of 4 to 5 with 20 g of formic acid. The white precipitate is filtered off, washed with water, and dried.

Weight: 102.0 g (95.4% of theory)
Melting point (sample recrystallized from ethyl alcohol): 136°–137.5° C.
Purity (HPLC): 98.1%.

EXAMPLE 5

Cyclopropyl-1,1-dicarboxylic acid monoethyl ester mono-(2,4-dichloro)-anilide ‖ [cyclopropyl-1-(2,4-dichlorophenylamino)-carbonyl-1-carboxylic acid ethyl ester] and its sodium salts and potassium salts 59. g (0.88 mole) of solid sodium methanolate, 500 ml cyclohexane, and 129.6 g (0.8 mole) of 2,4-dichloroaniline are heated to the boiling point in a 1.5-1 four-necked flask equipped with a thermometer, mixer, short column and distillation section. The batch is allowed to cool to room temperature. 148.9 g (0.8 mole) of cyclopropyl-1,1-dicarboxylic acid diethyl ester (CDE) are added. The batch is heated to the boiling point again and all the ethyl alcohol distilled off for 2 hours.

The batch is cooled and the precipitate—the sodium salt of cyclopropyl-1,1-dicarboxylic acid monoethyl ester mono-(2,4-dichloro)anilide)—filtered off and dried.

The total product is stirred in 1 l of cold water and acidified to a pH of 4 to 5 with formic acid. The resulting precipitate is filtered off, washed with water, and dried.

Weight: 201 g (83.2% of theory)
Melting point: 95°–97° C.
Purity (HPLC): 97.1%

The potassium salt is obtained similarly but with a 40% suspension by weight of KOC$_2$H$_5$ in ethyl alcohol.

Melting point: >200° C. (disintegration)

The free mono-ester mono-anilide is obtained at the aforesaid purity and melting point by dissolution in water and acidification with formic acid.

EXAMPLE 6

Cyclopropyl-1,1-dicarboxylic acid bis-(2,4-dichloro)-anilide [N,N'-bis-(2,4-dichlorophenyl)-cyclopropyl-1,1-dicarboxylic acid amide]

150 g (0.83 mole) of a. 30% solution of NaOCH$_3$ and 133 g (0.82 mole) of 2,4-dichloroaniline are dissolved in 500 ml of toluene in a four-necked flask equipped with a thermometer, mixer and distillation section. The azeotrope of methyl alcohol and toluene is distilled off at boiling heat- The batch is cooled to room temperature. 63.2 g (0.4 mole) of cyclopropyl-1,1-dicarboxylic acid dimethylester are added. The batch is allowed to stand for approximately 1 hour and heated to the boiling point for 1.5 hours, with the azeotrope being eliminated again. The batch is cooled and neutralized with formic acid. The precipitate is filtered out, washed with toluene and water, and dried.

Yield: 202 g (90% of theory)
Melting point: 158° C.
Purity (HPLC): 99% $C_{17}H_{12}Cl_4N_2O_2$

|        | C    | H   | N   | O   |
|--------|------|-----|-----|-----|
| Calc.: | 48.8 | 2.9 | 6.7 | 7.8 |
| Found: | 49.1 | 3.1 | 6.3 | 8.0 |

EXAMPLE 7

Cyclopropyl-1,1-dicarboxylic acid mono-anilide, cyclopropyl-1,1-dicarboxylic acid bis-anilide, and their sodium salts a) Prepared with NaOCH$_3$ 79.2 g (0.44 mole) of a 30% by weight solution of NaOCH$_3$ and 37.3 g (0.4 mole) of aniline are heated to the boiling point in 500 ml of cyclohexane. All the methyl alcohol is distilled off azeotropically. The batch is cooled to room temperature. 63.2 g (0.4 mole) of cyclopropyl-1,1-dicarboxylic acid dimethyl ester are added continuously. 30 minutes later the batch is heated to the boiling point and the methyl alcohol azeotrope distilled off. The batch is allowed to react for 2 hours and heated to the boiling point for 4 hours with 500 ml of water until the pH drops from an original 13–14 to 10–11. The batch is allowed to cool and the organic separated from the aqueous phase. The aqueous phase is filtered clear and acidified to a pH of 3 to 4 with formic acid. The resulting precipitate is filtered out, washed with water, and dried, yielding cyclopropyl-1,1-dicarboxylic acid mono-anilide.

Weight: 70.0 g (85.3% of theory)
Melting point after recrystallization from cyclohexane: 181°–182° C.
Purity (HPLC): 98.6% b) Preparation with potassium t-butylate

The reaction described in a) is carried out with 0.4 mole of aniline except that equivalent amounts of solid potassium t-butylate are employed instead of the NaOCH₃ solution and the same amount of toluene instead of the cyclohexane.

The batch is saponified with water. The toluene phase is separated from the aqueous phase. The resulting precipitate is filtered out, washed neutral with water, and dried, yielding cyclopropyl-1,1-dicarboxylic acid-bis-anilide.

Weight: 13.4 g (11.9% of theory)
Melting point: 212°–213.5° C.
Purity (HPLC): 97%

The filtered aqueous phase is acidified to a pH of 3 with hydrochloric acid. Cyclopropyl-1,1-dicarboxylic acid mono-anilide precipitates in a yield of more than 80%. The physical characteristics are the same as those listed in a).

Both the mono-acid mono-anilide obtained in a) and the bis-anilide obtained in b) are separately dissolved in water by heating with one or two equivalents of NaOH. The batches are chilled. Methyl alcohol is added. The monosodium salts and the disodium salts of the bis-anilide precipitate.

Melting point: >200° C. (disintegration)

The structure is demonstrated by precipitating the free compound from an aqueous solution with acid and determining the melting point.

EXAMPLES 8 TO 15

Cyclopropyl-1,1-dicarboxylic acid dimethyl ester was converted into the corresponding cyclopropyl-acid ester and cyclopropyl-acid anilides with 3,4-dichloroaniline (3,4-DCA), 2,6-dichloroaniline (2,6-DCA), 2,5-dichloroaniline (2,5-DCA), and 3-chloroaniline (3-CA) by the methods employed to prepare cyclopropyl-1,1-dicarboxylic acid monomethyl ester mono-(2,4-dichloro)-anilide (Example 4) and cyclopropyl-1,1-dicarboxylic acid mono-(2,4-dichloro)-anilide (Example 1).

The following table lists the melting points and gas-chromatography purities of the compounds.

| Ester acid | Ex. | Mp [°C.] | G.C.-purity. [%] |
|---|---|---|---|
| 3,4-Dichloranilide | | | |
| COOCH₃ / CO—x | 8 | 157–59 | 93[1] |
| COOH / CO—x | 9 | 219–21 | 98.1 |
| Recrystallization out of | | Toluene | |
| 2,6-Dichloranilide | | | |
| COOCH₃ / CO—x | 10 | 100–02 | 96.8 |
| COOH / CO—x | 11 | 237–39 | 97.0 |
| Recrystallization out of | | Toluene | |
| 2,3-Dichloranilide | | | |
| COOCH₃ / CO—x | 12 | 113–14 | 98.0 |
| COOH / CO—x | 13 | 220–22 | 97.0 |
| Recrystallization out of | | Toluene | |
| 3-Chloranilide | | | |
| COOCH₃ / CO—x | 14 | 82–85 | 96.1 |
| COOH / CO—x | 15 | 168–70 | 98.6 |
| Recrystallization out of | | Cyclohexane | | with corresponding acid components

EXAMPLE 16

Diethylmalonic acid monoethyl ester-(2,4-dichloro)-aniline 64.8 g (0.4 mole) of 2,4-dichloroaniline, 141.5 g (0.44 mole) of a 21.2% by weight solution of sodium methanolate in ethyl alcohol, and 500 ml of toluene are heated to the boiling point in an apparatus of the type described in Example 1. All the alcohol is distilled off. The batch is allowed to cool to room temperature. 86.5 g (0.4 mole) of diethyl malonate are added. The batch is stirred for 1 hour and slowly heated to 115° C. The reaction alcohol is distilled off at this reaction temperature in less than 3 hours. The batch is cooled to 80° C. and stirred up in toluene. The batch is cooled with formic acid (0.44 mole). Sodium formate crystallizes out. It is filtered out at 20° C. and the filtrate is distilled off through a column.

The toluene is picked up with a little foreshot. The product, diethylmalonic acid monoethyl ester-(2,4-dichloro)-anilide, distills over at 138° C. and 0.5 mbar.

Yield: 113.9 g (85.7 of theory)
Melting point: 26°–28° C.
Purity: 96% (gas. chr.) C₁₅H₁₉Cl₂NO₃ (MW 332.23)

| | C | H | Cl | N | O |
|---|---|---|---|---|---|
| Calc.: | 54.2 | 5.8 | 21.4 | 4.2 | 14.5 |
| Found: | 54.2 | 5.8 | 21.7 | 4.2 | 14.7 |

EXAMPLE 17

Diethylmalonic acid mono-(2,4-dichloro)-anilide 25 g (0.075 mole) of the diethylmalonic acid ethyl ester mono-(2,4-dichloro)-anilide prepared in Example 16 are heated to the boiling point for 4 to 5 hours with 42 g of 20% potassium hydroxide solution and 0.5 g of the phase-transfer catalyst Aliquat 336. A uniform phase occurs. The batch is cooled to room temperature and neutralized with formic acid. The precipitate is thoroughly mixed with water and then with heptane, filtered out, and washed.

Weight: 18 g (79% of theory)
Melting point: 82°–86° C.
Purity (HPLC): 96% (HPLC) $C_{12}H_{15}Cl_2NO_3$ (MW 304.17)

|  | C | H | Cl | N | O |
|---|---|---|---|---|---|
| Calc.: | 51.3 | 5.0 | 23.3 | 4.6 | 15.8 |
| Found: | 50.3 | 4.9 | 22.2 | 4.7 | 16.1 |

EXAMPLE 18

Diethylmalonic acid bis-(2,4-dichloro)-anilide 129.6 g (0.8 mole) of 2,4-dichloroaniline and 283 g (0.88 mole) of a 21 2% by weight solution of sodium ethanolate in ethyl alcohol was heated to the boiling point with 600 ml of toluene, distilling all the alcohol off. The batch was cooled to 70° C. 86.5 g (0.4 mole) of diethyl diethyl malonate are added drop by drop. The batch is heated to the boiling point for 7 hours, with the reaction alcohol being picked up. The batch is cooled, treated with 500 ml of water, and neutralized while agitated with 41 g (0.88 mole) of formic acid. The aqueous phase is separated and the toluene phase concentrated to dryness. An oil-pump vacuum of 0.5 mbar is generated to distill the unsaponified diethylmalonic acid ethyl ester mono-(2,4-dichloro)-anilide. The distillation residue is recrystallized from heptane.

Melting point: 127°–128° C.
Purity (HPLC): 98% $C_{19}H_{18}Cl_4N_2O_2$ (MW 448.18)

|  | C | H | N |
|---|---|---|---|
| Calc. | 50.9 | 4.1 | 6.1 |
| Found | 50.3 | 4.2 | 6.1 |

EXAMPLE 19

Ethylmalonic acid mono-(2,4-dichloro)-anilide 64.8 g (0.4 mole) of 2,4-dichloroaniline are dissolved in 142 g (0.44 mole) of a 21.2% by weight solution of sodium ethanolate in ethyl alcohol. 500 ml of toluene are added. The batch is brought to the boil, with the ethyl alcohol being distilled off.

The batch is cooled to room temperature. 75.3 g (0.4 mole) of ethylmalonic acid diethyl ester are added. The mixture is left at room temperature for 1 hour and heated for 1.5 hours to the boiling point, with all the reaction alcohol again being distilled off azeotropically.

The batch is allowed to cool, and 500 ml of water are added. The batch is again heated to boiling and the toluene distilled off azeotropically. The batch is filtered clear, and the filtrate acidified to a pH of 3 with hydrochloric acid. The resulting precipitate is filtered out, washed with water, and dried.

Weight: 79.6 g (72.14 of theory)
Melting point: 141°–142° C.
Purity (HPLC): 99.4% $C_{11}H_{11}Cl_2NO_3$ (MW 276.12)

|  | C | H | Cl | N | O |
|---|---|---|---|---|---|
| Calc.: | 47.9 | 4.0 | 25.7 | 5.1 | 17.4 |
| Found: | 47.7 | 4.3 | 26.5 | 4.8 | 18.1 |

EXAMPLE 20

Ethylmalonic acid monoethyl ester-(2,4-dichloro)-anilide

Example 19 is repeated exactly with the exception that the procedure subsequent to the formation of the anilide is as follows:

The toluene solution is neutralized with a stoichiometric amount of concentrated formic acid. The precipitated sodium formate is filtered out and the filtrate concentrated to dryness, yielding 116.7 g (95.9% of theory).

This residue is dissolved in warm cyclohexane. An insoluble precipitate, ethylmalonic acid bis-(2,4-dichloro)-anilide, is filtered off. The cyclohexane filtrate is concentrated and cold crystallized. The crystals are filtered, washed with heptane, and dried.

Melting point: 54°–57° C.
Purity (HPLC): 96% (gas chr.) $C_{13}H_{15}Cl_2NO_3$ (MW 304.17)

|  | C | H | Cl | N | O |
|---|---|---|---|---|---|
| Calc.: | 51.3 | 4.9 | 23.3 | 4.6 | 15.7 |
| Found: | 50.4 | 4.8 | 24.2 | 4.5 | 15.3 |

EXAMPLE 21

Ethylmalonic acid bis-(2,4-dichloro)-anilide

The procedure described in Example 19 is followed, except that 129.6 g (0.8 mole) of 2,4-dichloroaniline, 283 g (0.88 mole) of a 21.2% by weight solution of sodium ethanolate in ethyl alcohol, and 75.2 g (0.4 mole) of ethylmalonic acid diethyl ester are reacted in 500 ml of toluene. All the alcohol is distilled off and the reaction mixture cooled.

The toluene phase is decanted from the resulting precipitate. The precipitate is stirred up in water to which an equivalent amount of formic acid has been added. The accordingly neutralized product is filtered and washed twice with water and acetone alternately, filtered and washed again, and dried.

Melting point: 201°–203° C.
Purity (HPLC): 96% $C_{17}H_{14}Cl_4N_2O_2$ (MW 420.13)

|  | C | H | N |
|---|---|---|---|
| Calc.: | 48.6 | 3.3 | 6.7 |
| Found: | 48.1 | 3.5 | 6.3 |

EXAMPLE 22

The sodium salt of 2,4-dichloroaniline 40.0 g (0.246 mole) of 2,4-dichloroaniline, 44.2 g (0.246 mole) of a 30% by weight solution of sodium methanolate in methyl alcohol, and 300 ml of cyclohexane are placed in a 1—1 multiple-neck flask and heated to the boiling point, with the methyl alcohol being picked up as an azeotrope. All the alcohol is distilled off. The crystallized precipitate is filtered out, washed with cyclohexane, and dried.

Yield: 41 g (90.5% of theory)
Melting point: >200° C.

Na

Calc. 12.5%
Found 12.6%

EXAMPLE 23

The potassium salt of 2,4-dichloroaniline

The potassium salt was obtained in a yield of over 90% by proceeding as described in Example 22 but with the equivalent amount of a potassium methanolate solution.
Melting point: >200° C.
Potassium, as calculated.

EXAMPLE 24

The sodium and potassium salts of 3-chloroaniline, 3,4-dichloroaniline, and 2,6-dichloroaniline were prepared by the procedure described in Example 22.
Melting point: >200° C.
Sodium and potassium, as calculated.

It will be understood that the specification and examples are illustrative but not limitative of the present invention and that other embodiments within the spirit and scope of the invention will suggest themselves to those skilled in the art.

I claim:

1. In the preparation of a mono-ester mono-amide, mono-acid mono-amide or bis-amide of a singly or doubly substituted malonic acid, of the formula

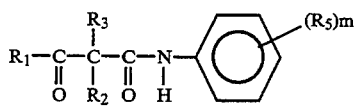 (I)

or a mixture thereof, wherein a singly or doubly substituted malonic acid dialkyl ester of the formula

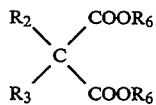 (II)

is reacted with an aniline of the formula

 (III)

wherein
$R_1$ = O-alkyl ($C_1$–$C_6$) OH, O$^-$ alkali$^+$, or

, $R_2$ = alkyl ($C_1$–$C_6$), alkoxy ($C_1$–$C_6$), or aryl,
$R_3$ = H, alkyl ($C_1$–$C_6$), alkoxy ($C_1$–$C_6$), or aryl, or
$R_2$+$R_3$ = —($R_4CR_4$)$_n$—, where n=2–5
$R_4$ = H, $CH_3$, or halogen,
$R_5$ = halogen, alkyl ($C_1$–$C_6$), alkoxy ($C_1$–$C_6$), N($R_6$)$_2$, cyano, acyl, nitro, or thioalkyl ($C_1$–$C_6$),
m = 0–5, and
$R_6$ = alkyl ($C_1$–$C_6$),
the improvement which comprises
a) effecting the reaction in the presence of a stoichiometric amount of an alkali alcoholate based on the aniline (III),
b) neutralizing the reaction product with an acid thereby to produce the malonic mono-ester mono-anilide and malonic bis-anilide, and
c) reacting the product with water thereby to saponify the ester group in the reaction mixture to produce the mono-anilide.

2. A process according to claim 1, wherein the alkali alcoholate is employed in about 85% to 130% based on the stoichiometric amount relative to the amine (III).

3. A process according to claim 1, wherein the alkali alcoholate is employed in about 95% to 110% based on the stoichiometric amount relative to the amine (III).

4. A process according to claim 1, wherein the alkali alcoholate is introduced into the reaction mass in solid form.

5. A process according to claim 1, wherein the alkali alcoholate is introduced into the reaction mass dissolved in an alcohol.

6. A process according to claim 1, wherein the alkali alcoholate is prereacted with the aniline, the malonic acid ester is then added and the reaction is carried forward.

7. A process according to claim 1, wherein the reaction is effected in solution in an inert aliphatic or aromatic hydrocarbon.

8. A process according to claim 1, wherein the reaction is effected at a temperature up to 150° C.

* * * * *